(12) United States Patent
Hodgson et al.

(10) Patent No.: US 10,689,316 B2
(45) Date of Patent: Jun. 23, 2020

(54) PROCESS FOR THE PREPARATION OF 3,3,3-TRIFLUOROPROPENE

(71) Applicant: MEXICHEM FLUOR S.A. DE C.V., San Luis Potosi (MX)

(72) Inventors: Emma Jayne Hodgson, Cheshire (GB); Claire Elizabeth McGuinness, Cheshire (GB); Clive Robert Giddis, Cheshire (GB); James Henry Murray, Cheshire (GB); Clare Mary Skae, Cheshire (GB); Gary Lloyd, Cheshire (GB)

(73) Assignee: MEXICAN FLUOR S.A. DE C.V., San Luis Potosi (MX)

( * ) Notice: Subject to any disclaimer, the term of this patent is extended or adjusted under 35 U.S.C. 154(b) by 0 days.

(21) Appl. No.: 15/745,460

(22) PCT Filed: Jul. 14, 2016

(86) PCT No.: PCT/GB2016/052137
§ 371 (c)(1),
(2) Date: Jan. 17, 2018

(87) PCT Pub. No.: WO2017/013404
PCT Pub. Date: Jan. 26, 2017

(65) Prior Publication Data
US 2019/0169098 A1 Jun. 6, 2019

(30) Foreign Application Priority Data
Jul. 17, 2015 (GB) .................. 1512598.2

(51) Int. Cl.
*C07C 17/25* (2006.01)
*C07C 17/35* (2006.01)
*C07C 17/07* (2006.01)
*C09K 5/04* (2006.01)

(52) U.S. Cl.
CPC ............. *C07C 17/25* (2013.01); *C07C 17/07* (2013.01); *C07C 17/35* (2013.01); *C09K 5/04* (2013.01)

(58) Field of Classification Search
CPC ......... C07C 17/25; C07C 17/07; C07C 17/35; C07C 19/10; C07C 21/18; C07C 17/20; C07C 17/38; C09K 5/04; B01J 37/26; B01J 23/44; B01J 23/42; B01J 23/26; B01J 23/06; B01J 21/18
USPC ...................................................... 252/67
See application file for complete search history.

(56) References Cited

U.S. PATENT DOCUMENTS

| | | | | |
|---|---|---|---|---|
| 2,889,379 A | * | 6/1959 | Davis | C07C 17/00 570/160 |
| 4,078,007 A | | 3/1978 | Ferstandig | |
| 4,220,608 A | * | 9/1980 | Feiring | C07C 17/00 570/155 |
| 4,465,786 A | * | 8/1984 | Zimmer | B01J 27/06 502/169 |
| 4,766,258 A | | 8/1988 | Komatsu et al. | |
| 5,066,418 A | * | 11/1991 | Merchant | C11D 7/5059 134/12 |
| 5,227,088 A | | 7/1993 | Swan et al. | |
| 5,986,151 A | * | 11/1999 | Van Der Puy | C07C 17/25 570/156 |
| 6,235,161 B1 | | 5/2001 | Crooker et al. | |
| 2002/0142927 A1 | | 10/2002 | Pham et al. | |
| 2006/0217578 A1 | | 9/2006 | Rao et al. | |
| 2012/0071699 A1 | * | 3/2012 | Sharratt | C07C 17/206 570/158 |
| 2013/0102815 A1 | * | 4/2013 | Smith | C07C 17/04 570/166 |
| 2019/0330130 A1 | * | 10/2019 | Johnson | C07C 17/25 |

FOREIGN PATENT DOCUMENTS

| | | | |
|---|---|---|---|
| CN | 1488614 A | * | 4/2004 |
| CN | 103044191 | | 4/2013 |
| EP | 0502605 | | 9/1992 |
| EP | 0773061 | | 5/1997 |
| EP | 0957074 | | 11/1999 |
| JP | S5246004 | | 4/1977 |
| JP | S61267533 | | 11/1986 |
| JP | H0625027 | | 2/1994 |
| JP | 2004526696 | | 9/2004 |
| JP | 2007508376 | | 4/2007 |
| WO | WO1998/010862 | | 3/1998 |
| WO | WO2008/040909 | | 4/2008 |
| WO | WO2009/125199 | | 10/2009 |
| WO | WO2009/125200 | | 10/2009 |
| WO | WO 2009/125201 | | 10/2009 |
| WO | WO2010/116150 | | 10/2010 |
| WO | WO2015/092211 | | 6/2015 |

OTHER PUBLICATIONS

International Search Report pertaining to PCT/GB2016/052137, dated Sep. 11, 2016, 5 pages.
Written Opinion of the International Search Authority pertaining to PCT/GB2016/052137, dated Sep. 11, 2016; 9 pages.
Joyce et al., Free Radical-initiated Reaction of Ethylene with Carbon Tetrachloride; J. Am. Chem. Soc., vol. 70, pp. 2529-2532; Jul. 1948.

\* cited by examiner

*Primary Examiner* — Douglas J McGinty
(74) *Attorney, Agent, or Firm* — Ryan Kromholz & Manion, S.C.

(57) ABSTRACT

The present invention provides a process for preparing 3,3,3-trifluoropropene (1243zf), the process comprising: (a) fluorinating $CCl_3CH_2CH_2Cl$ (250fb) to produce a reaction product comprising $CF_3CH_2CH_2Cl$ (253fb) in the liquid phase in a first reactor, using HF as the fluorinating agent; and (b)(i) dehydrohalogenating 253fb to produce 1243zf in the vapour phase in the presence of a catalyst in a second reactor; or (b)(ii) dehydrohalogenating 253fb to produce 1243zf in a second reactor, wherein the reaction product comprising 253fb produced in step (a) has subjected to one or more purification steps before step (b). The present invention also provides an azeotropic or near-azeotropic composition comprising HF and 253fb.

24 Claims, 2 Drawing Sheets

PROCESS FOR THE PREPARATION OF 3,3,3-TRIFLUOROPROPENE

The invention relates to a process for preparing 3,3,3-trifluoropropene.

3,3,3-trifluoropropene, which is also known as HFO-1243zf (or 1243zf), is a useful monomer for the production of fluorosilicones, and in the manufacture of trifluoropropene epoxide and 3,3,3-trifluoropropylbenzene. 1243zf is also believed to have utility in refrigerant compositions.

The listing or discussion of a prior-published document in this specification should not necessarily be taken as an acknowledgement that the document is part of the state of the art or is common general knowledge.

U.S. Pat. No. 5,986,151 describes the preparation of 1243zf starting from $CF_3CH_2CF_2H$, involving a complicated series of separate dehydrofluorination and hydrogenation reactions.

U.S. Pat. No. 4,220,608 describes the preparation of 1243zf by reacting at least one of 1,1,1,3-tetrachloropropane (also known as 250fb), 1,1,3-trichloroprop-1-ene and 3,3,3-trichloropropene with hydrogen fluoride (HF) in the presence of a nitrogen-based catalyst. Such catalysts are not ideal, for example because they cannot easily be regenerated or separated from the reagents and/or products.

U.S. Pat. Nos. 2,889,379 and 4,465,786 both describe the preparation of 1243zf by the reaction of a halogenated hydrocarbon (e.g. 250fb) with HF in the presence of (modified) chromium oxyfluoride catalysts. The activity, selectivity, robustness and/or ease of regeneration of such catalysts are not ideal.

The subject invention addresses the above and other deficiencies in the art by the provision of a process for preparing 3,3,3-trifluoropropene (1243zf), the process comprising:
(a) fluorinating $CCl_3CH_2CH_2Cl$ (250fb) to produce $CF_3CH_2CH_2Cl$ (253fb) in the liquid phase in a first reactor; and
(b) dehydrohalogenating 253fb to produce 1243zf in the vapour phase in the presence of a catalyst in a second reactor.

The present invention also provides a process for preparing 3,3,3-trifluoropropene (1243zf), the process comprising:
(a) fluorinating $CCl_3CH_2CH_2Cl$ (250fb) to produce a reaction product comprising $CF_3CH_2CH_2Cl$ (253fb) in the liquid phase in a first reactor, using HF as the fluorinating agent; and
(b) dehydrohalogenating 253fb to produce 1243zf in a second reactor;
wherein the reaction product comprising 253fb produced in step (a) is subjected to one or more purification steps before step (b).

250fb may be purchased from common suppliers of halogenated hydrocarbons, such as Apollo Scientific, Stockport, UK. Alternatively, 250fb may be prepared by the telomerisation of carbon tetrachloride ($CCl_4$) and ethylene (see, for example, J. Am. Chem. Soc. Vol. 70, p 2529, 1948, which is incorporated herein by reference).

The conversion of 250fb to 1243zf typically involves fluorination and dehydrohalogenation steps.

For example, 250fb may be fluorinated to produce $CF_3CH_2CH_2Cl$, as illustrated in the scheme below. 1243zf may be produced by a final dehydrochlorination step of $CF_3CH_2CH_2Cl$. This is illustrated below:

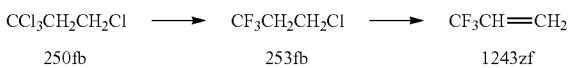

$CCl_3CH_2CH_2Cl \longrightarrow CF_3CH_2CH_2Cl \longrightarrow CF_3CH=CH_2$
250fb           253fb           1243zf Step (a) of the process of the invention is typically conducted at a temperature of from about 20 to about 100° C., preferably from about 40 to about 70° C.

Step (a) is typically conducted at a pressure of from about 100 to about 1000 kPa (about 1 to about 10 barg), preferably from about 200 kPa to about 700 kPa (about 2 to about 7 barg).

In one aspect, step (a) may be conducted at a temperature of from about 40 to about 70° C. and a pressure of from about 200 kPa to about 700 kPa.

Step (a) may be conducted in the presence of a polymerisation inhibitor and/or retarder. Any suitable polymerisation inhibitor/retarder may be used. Suitable polymerisation inhibitors include, but are not limited to, cyclic ketone or quinone-based aromatic compounds, nitro- or nitrogen-containing compounds, or sulphur-containing compounds, e.g. cyclobutanone and cyclohexanone and mixtures thereof. Without wishing to be bound by theory, it is believed that the use of a polymerisation inhibitor/retarder minimises tar formation.

Step (a) is typically conducted in the presence of a catalyst. Suitable catalysts include Lewis acid catalysts. Suitable Lewis acid catalysts include, but are not limited to, $TiCl_4$, $BF_3$, $SnF_xCl_y$ (wherein x+y=4) such as $SnCl_4$ or $SnCl_2F_2$, $TaF_5$, $SbCl_5$ and $AlCl_3$. A preferred catalyst for use in step (a) is $SnF_xCl_y$.

$SnCl_4$ is readily available. $SnCl_4$ will be fluorinated in the presence of HF to form mixed Cl/F species and/or $SnF_4$. Therefore, in one aspect of the invention, the catalyst (eg $SnCl_4$) may be charged to the reactor and treated with a known volume of HF to fluorinate the catalyst prior to the start of the reaction; for example prior to any continuous feed of the reagents for step (a). During this pre-fluorination step, any HCl generated can be removed from the reactor.

The concentration of the catalyst can vary within wide limits. As a non-limiting example, the catalyst concentration may be from about 10 to about 25 wt % in HF, such as from about 15 to about 20 wt % in HF Step (a) is preferably conducted in a non-aqueous or anhydrous environment. It is therefore preferable to use anhydrous HF in step (a).

The ratio of HF to 250fb in step (a) can vary within wide limits. The ratio of HF to 250fb may, for example, be from about 1:1 to about 20:1, such as about 5:1 to about 15:1, for example about 10:1.

250fb is typically fed into the reactor for step (a) in the liquid phase.

Step (a) can be conducted as a batch reaction, a continuous reaction or as a semi-continuous reaction. Use of a semi-continuous reaction is preferred because this allows for purging/cleaning and replacement of the catalyst as necessary.

An example of a possible arrangement of reactors of semi-continuous operation of step (a) is to use 2 or more, for example, 3, 4 or 5 reactors in parallel arranged so that each of the reactors may be independently switched off and isolated to allow purging and/or cleaning while the other reactor(s) continue to operate.

For example, 3 reactors, such as 3 reactors each with a volume of from about 5 $m^3$ to about 15 $m^3$, for example, about 10 $m^3$ may be used to carry out step (a). In this arrangement, the reaction rate may be approximately 150 to 350 kg/m³h, such as approximately 200 to 300 kg/m³h. It is expected that with this arrangement, it will be necessary to purge/clean the reactor(s) every 3 to 10 days, for example about every 4 or 5 days.

Any suitable reactor may be used for step (a). An example of a suitable reactor is a steady state, continuously stirred tank reactor.

In one advantageous arrangement, the reactor(s) used for step (a) may be connected to a rectifying column(s). Lighter compounds such as unused HF, 253fb and HCl generated during the reaction leave the reactor(s) via the rectifying column(s), while heavier compounds remain in the reactor(s). In this arrangement, intermediates and/or by-products, such as 251fb ($CH_2ClCH_2CCl_2F$) or 252fc ($CClF_2CH_2CH_2Cl$) may be condensed in the rectifying column and thus be returned to the reactor, where they may be fluorinated further.

In one particular arrangement, the HF fed may be introduced into the reactor via the top of the rectifying column. Without wishing to be bound by theory, it is believed that this can reduce fouling within the column by lowering organics concentrations.

The product stream exiting the step (a) reactor, for example via the rectifying column, can be subjected to one or more separation and/or purification steps before being passed to the second reactor or before being stored prior to passing to the second reactor. Alternatively, the product stream may be passed directly to the second reactor or may be stored without being subjected to separation and/or purification.

If the product stream from the step (a) reactor is subjected to separation and/or purification any suitable separation and/or purification techniques may be used. Suitable techniques include, but are not limited to distillation, phase separation, scrubbing and adsorption, eg using molecular sieves and/or activated carbon.

The product stream from the step (a) reactor may be subjected to distillation to separate HCl from the HF and organics. The HCl may then be recovered.

HF can be separated from a product stream comprising 253fb by, for example, phase separation and/or use of an acid scrubber such as a $H_2SO_4$ scrubber, for example a $H_2SO_4$ scrubber operated above ambient temperature. HF separated in this way can be recycled back into the step (a) reactor. If an acid scrubber is used, the product stream comprising 253fb may be passed through a molecular sieve or a sofnolime packed bed to remove traces of acid.

In an example of purification process that may be used in the present invention, the product stream from step (a) may be subjected to distillation to remove or reduce the concentration of HCl and then phase separation to separate the HF from the product stream comprising 253fb (the organics). The product stream may then optionally be passed through a $H_2SO_4$ scrubber.

The product stream may optionally be cooled before being subjected to phase separation or the phase separation may take place at or below ambient temperature.

The 253fb produced in step (a) may be condensed and stored, for example in a buffer tank, prior to use in step (b).

It has been found by the inventors that an HF/253fb azeotrope or near-azeotrope may be present in the product stream produced in step (a).

By azeotrope or azeotropic composition, we mean a binary composition which at vapour-liquid equilibrium has the same composition in both the liquid and vapour phase, and whose boiling point is lower than that of either of the pure components. By near-azeotrope or near-azeotropic composition (e.g. a near-azeotropic composition of 253fb and HF), we mean a composition that behaves similarly to an azeotrope composition (i.e. the composition has constant boiling characteristics or a tendency not to fractionate upon boiling), but may not have all of the properties of an azeotrope, for example binary liquid compositions whose vapour pressure is above that of the pure component with the lower boiling point (e.g. HF compared to 253fb) when measured at equivalent temperature, but whose equilibrium vapour composition may differ from the liquid composition.

In essence, at a given pressure, a boiling azeotrope or near azeotrope composition has the same constituent proportions in the vapour phase as in the boiling liquid phase. This means that no (or substantially no) fractionation of the components in the liquid composition takes place.

In the present invention, upon formation of the reaction product 253fb in step (a), HF may be present in an effective amount to form an azeotropic composition with 253fb. By effective amount, it is meant that HF and 253fb are present in suitable ratios in order to form azeotrope or near azeotrope compositions.

A binary azeotrope composition has been identified between HF and R253fb (see FIGS. 1 to 3). Compositions comprising from about 65 mol % to about 90 mol % HF and from about 35 mol % to about 10 mol % 253fb have been shown to form azeotropes at temperatures of from about −25° C. to about +70° C., such as compositions comprising from about 70 mol % to about 85 mol % of HF and from about 30 mol % to about 15 mol % of 253fb.

Additionally, near azeotrope compositions have been identified between HF and R253fb, wherein HF is present in an amount of from about 55 mol % to about 95 mol % and 253fb is present in an amount of from about 45 mol % to about 5 mol %. Such near-azeotrope compositions exist across temperatures ranging from about −25° C. to about +70° C.

For example, it has been found that a composition consisting of about 75 mol % HF and about 25 mol % 253fb is azeotropic at 70° C. and 600 kPa (6 bara)

The present inventors have also found that phase separation, for example phase separation at temperatures below approximately 30° C. can be used to separate the HF and 253fb in the azeotropic or near-azeotropic composition. The HF phase separated may comprise 88 to 100 mol % HF, such as about 90 mol % HF. This separation step enables the HF to be recycled to step (a).

In one aspect of the invention, step (b), 253fb is dehydrochlorinated to produce 1243zf in the vapour phase in the presence of a catalyst. A process in which the product stream from reaction (a) is purified as described above before 253fb is dehydrochlorinated to produce 1243zf in the vapour phase in the presence of a catalyst is envisaged.

When step (b) is conducted in the vapour phase in the presence of a catalyst any suitable catalyst may be used. Suitable catalysts may comprise activated carbon, alumina and/or chromia or zinc/chromia. Examples of suitable catalyst include activated carbon, Pt/carbon, Pd/carbon, Au/carbon, Pd/alumina, Ni/alumina, Pt/alumina, Cr/alumina or Zn/chromia.

The inventors have found that the use of a catalyst in step (b) in the vapour phase enables the dehydrohalogenation step to be conducted using less forcing conditions (e.g. lower temperature and/or pressure and/or residence time) than would otherwise be necessary.

Catalysts suitable for use in step (b) in the vapour phase in the present invention can be obtained from commercial sources.

By the term "zinc/chromia catalyst" we mean any catalyst comprising chromium or a compound of chromium and zinc or a compound of zinc. Such catalysts are known in the art, see for example EP-A-0502605, EP-A-0773061, EP-A-0957074 and WO 98/10862, which are incorporated by reference herein.

Typically, the chromium or compound of chromium present in the zinc/chromia catalysts of the invention is an oxide, oxyfluoride or fluoride of chromium such as chromium oxide.

The total amount of the zinc or a compound of zinc present in the zinc/chromia catalysts of the invention is typically from about 0.01% or about 0.5% to about 25%, preferably 0.1% or about 1% to about 10%, from about 2 to 8% by weight of the catalyst, conveniently 0.01% to 6% zinc, for example about 4 to 6% by weight of the catalyst.

It is to be understood that the amount of zinc or a compound of zinc quoted herein refers to the amount of elemental zinc, whether present as elemental zinc or as a compound of zinc.

The zinc/chromia catalysts used in the invention may include an additional metal or compound thereof. Typically, the additional metal is a divalent or trivalent metal, preferably selected from nickel, magnesium, aluminium and mixtures thereof. Typically, the additional metal is present in an amount of from 0.01% by weight to about 25% by weight of the catalyst, preferably from about 0.01 to 10% by weight of the catalyst. Other embodiments may comprise at least about 0.5% by weight or at least about 1% weight of additional metal.

When step (b) is conducted in the vapour phase in the presence of a catalyst, this step is typically conducted at a temperature of from about 150° C. to about 450° C., such as from about 150° C. to about 400° C., e.g. from about 200° C. to about 350° C., or from about 150° C. to about 250° C.

For example, the catalyst used in step (b) may comprise activated carbon and the process of step (b) may be conducted at a temperature from about 250° C. to about 350° C., preferably 250° C. to about 300° C.

In the process of the invention, the catalyst used in step (b) may be pre-fluorinated, i.e. fluorinated prior to use. Any suitable pre-fluorination technique may be used, for example, the catalyst may be pre-fluorinated by passing HF over the catalyst prior to the catalyst being contacted with 253fb.

For example, the catalyst used in step (b) may be a pre-fluorinated Zn/chromia catalyst, such as pre-fluorinated ZnO/Cr$_2$O$_3$, and the process of step (b) may be conducted at a temperature from about 250° C. to about 350° C.

In the process of the invention, step (b) may also be conducted by co-feeding the HF and 253fb feeds. For example, the catalyst used in step (b) may be pre-fluorinated, such as a pre-fluorinated ZnO/Cr$_2$O$_3$ catalyst, and HF and 253fb co-fed over the pre-fluorinated catalyst.

If the product stream from reaction (a) is purified as described above between step (a) and (b), step (b) may alternatively be conducted in the liquid phase or in the vapour phase in the presence of an inert material such as porcelain, quartz, alumina or Inconel mesh to aid heat transfer. Step (b) may, for example, be a thermal dehydrochlorination reaction conducted in the absence of a catalyst.

If step (b) is a thermal dehydrochlorination reaction this reaction is typically conducted at a temperature of from about 300 to about 800° C., such as from about 400 to about 600° C., eg from about 450 to about 550° C.

When step (b) is conducted in the vapour phase, it is typically conducted at atmospheric, sub- or super atmospheric pressure, such as at a pressure of from about 0 kPa to about 3000 kPa (about 0 to 30 barg), preferably from about 100 kPa to about 200 kPa (about 1 to about 20 barg).

The reaction time for the 1243zf preparation process (step (b)) is generally from about 1 second to about 100 hours, preferably from about 10 seconds to about 50 hours, such as from about 1 minute to about 10 or 20 hours in the vapour phase.

In a continuous process, typical contact times of the catalyst with the reagents is from about 1 to about 1000 seconds, such from about 1 to about 500 seconds or about 1 to about 300 seconds or about 1 to about 50, 100 or 200 seconds.

If step (b) is conducted in the liquid phase it is typically conducted in an aqueous environment in basic conditions. Any suitable base may be used to provide the basic environment. For example, aqueous NaOH may be used at a concentration of from about 10 to about 30 wt %. The liquid phase reaction typically takes place in the presence of a catalyst such as a phase transfer catalyst. Suitable phase transfer catalysts include quaternary ammonium salts such as dodecyltrimethylammonium chloride.

The liquid phase reaction (b) is typically conducted at a temperature of from about 30 to about 100° C., for example from about 50 to about 80° C. and a pressure of from about 100 kPa to about 300 kPa (about 1 to about 3 barg)

The dehydrohalogenation step can be carried out in any suitable apparatus, such as a static mixer, a stirred tank reactor or a stirred vapour-liquid disengagement vessel. Preferably, the apparatus is made from one or more materials that are resistant to corrosion, e.g. Hastelloy®, Inconel® or a fluoropolymer lined vessel.

The dehydrohalogenation step may be carried out batchwise or (semi-)continuously. Preferably, the step is carried out continuously.

The product stream exiting the step (b) reactor can be subjected to one or more separation and/or purification steps.

If the product stream from the step (b) reactor is subjected to separation and/or purification any suitable separation and/or purification techniques may be used. Suitable techniques include, but are not limited to distillation, phase separation, scrubbing and adsorption, eg using molecular sieves and/or activated carbon.

In one purification method, the product stream from the step (b) reactor is subjected to one or more distillation steps. For example, the product stream from the step (b) reactor may be subjected to three distillation steps. A first distillation step may be used to separate HCl for recovery. A second distillation step may be used to remove light by-products. A third distillation step may be used to separate out unreacted 253fb from the product; the unreacted 253fb can be recycled back into the step (b) reactor.

The 1243zf product can be stored for future use or can be passed directly into a further reactor.

Figure 1:
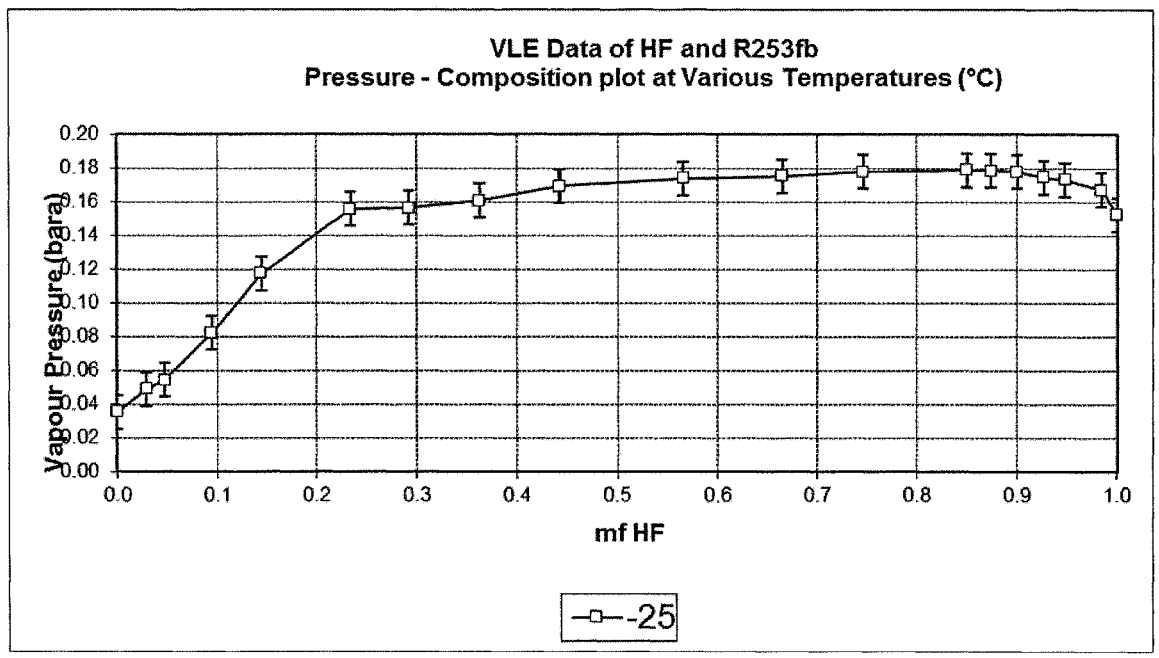
FIGS. 1 to 3 show the results obtained when measuring the vapour pressure of varying compositions of HF and 253fb over a temperature range of −25° C. to +70° C. The invention will now be illustrated with the following non-limiting examples.

The invention will now be illustrated by the following non-limiting Examples.

EXAMPLE 1

Catalytic (Activated Carbon) Dehydrochlorination of 253fb

The carbon-based catalysts in Table 1 were ground to 0.5-1.4 mm and 2 mL charged to an Inconel 625 reactor (0.5" OD×32 cm) supported by Inconel mesh. The catalysts were pre-dried at 200° C. for at least 2 hours under a flow of $N_2$ (60 ml/min) at atmospheric pressure then the reactor temperature was increased to 250° C. and the nitrogen reduced to 30 ml/min and diverted to the reactor exit. A flow of 253fb (3-chloro-1,1,1-trifluoropropane, 99.09%) was fed over the carbon catalysts by sparging liquid 253fb at 10° C. with 4-6 ml/min nitrogen, yielding 253fb vapour flows of 1-2.5 ml/min. After allowing the reaction to run for 30 min, reactor off-gases were sampled into deionised water and analysed by GC, to give the conversion of 253fb and selectivity to 1243zf results shown in Table 1. The experiment was also repeated at 300 and 350° C. for selected catalysts.

250° C. A flow of 253fb (3-chloro-1,1,1-trifluoropropane, 99.09%) was fed over the catalyst by sparging liquid 253fb at 10° C. with 10-12 ml/min nitrogen, yielding 253fb vapour flows of 4-5 ml/min. After allowing the reaction to run for 30 min, reactor off-gases were sampled into deionised water and analysed by GC, to give the conversion of 253fb and selectivity to 1243zf results shown in Table 2. The experiment was also repeated at 300 and 350° C.

Pre-Fluorinated:

HF at 30 ml/min was passed over the catalyst along with 60 ml/min nitrogen at 300° C. for one hour. The nitrogen flow was then directed to the reactor exit leaving neat HF passing over the catalyst. The temperature was slowly ramped to 360° C. and held for 10 hours. After this time the temperature was reduced to 300° C. and the flow of HF stopped and replaced with 30 ml/min nitrogen, for 1 h. The flow of nitrogen was then diverted to the reactor exit then a flow of 253fb (3-chloro-1,1,1-trifluoropropane, 99.09%) was fed over the catalyst by sparging liquid 253fb at 10° C. with 10-12 ml/min nitrogen, yielding 253fb vapour flows of 4-5 ml/min. After allowing the reaction to run for 30 min,

TABLE 1

Results for 253fb dehydrochlorination to 1243zf with activated carbon catalysts

| Catalyst | TR Ref # | 250° C. 253fb Conversion % | 250° C. 1243zf Selectivity % | 300° C. 253fb Conversion % | 300° C. 1243zf Selectivity % | 350° C. 253fb Conversion % | 350° C. 1243zf Selectivity % |
|---|---|---|---|---|---|---|---|
| Act. Carbon | 2367 | 9.82 | 100.00 | 37.23 | 100.00 | | |
| Act. Carbon | 2091 | 17.12 | 100.00 | 64.24 | 100.00 | | |
| Act. Carbon | 2032 | 26.10 | 100.00 | 73.01 | 100.00 | | |
| Act. Carbon | 1968 | 55.37 | 100.00 | 96.87 | 100.00 | | |
| Act. Carbon | 2019 | 20.03 | 100.00 | 66.12 | 100.00 | | |
| Act. Carbon | 2366 | 64.60 | 100.00 | 93.25 | 100.00 | 96.99 | 99.55 |
| 1.5% Pd/Carbon | 2630 | 14.06 | 100.00 | 17.87 | 97.79 | 36.62 | 33.77 |
| 0.8% Pd/Carbon | 2629 | 48.53 | 100.00 | 93.08 | 100.00 | 88.69 | 97.23 |
| 0.3% Au/Carbon | 2634 | 47.09 | 100.00 | 94.60 | 99.40 | | |

EXAMPLE 2

Catalytic Dehydrochlorination of 253fb Investigating the Effect of Pre-Fluorination, with/without HF Co-Feed on ZnO/Cr$_2$O$_3$ A ZnO/Cr$_2$O$_3$ catalyst was ground to 0.5-1.4 mm and 2 mL charged to an Inconel 625 reactor (0.5" OD×32 cm) supported by Inconel mesh. The catalyst was pre-dried at 200° C. for at least 2 hours under a flow of $N_2$ (60 ml/min) at atmospheric pressure. Three experiments carried out in duplicate were as follows:

Without Pre-Fluorination:

The nitrogen flow was reduced to 30 ml/min and diverted to the reactor exit and the reactor temperature increased to 250° C. A flow of 253fb (3-chloro-1,1,1-trifluoropropane, 99.09%) was fed over the catalyst by sparging liquid 253fb at 10° C. with 10-12 ml/min nitrogen, yielding 253fb vapour flows of 4-5 ml/min. After allowing the reaction to run for 30 min, reactor off-gases were sampled into deionised water and analysed by GC, to give the conversion of 253fb and selectivity to 1243zf results shown in Table 2.

Pre-Fluorinated and HF Co-Feed:

Pre-fluorination as described above. After this time the temperature was reduced to 250° C. and the flow of HF maintained over the catalyst. A flow of 253fb (3-chloro-1,1,1-trifluoropropane, 99.09%) was fed over the catalyst by sparging liquid 253fb at 10° C. with 10-12 ml/min nitrogen, yielding 253fb vapour flows of 4-5 ml/min. After allowing the reaction to run for 30 min, reactor off-gases were sampled into deionised water and analysed by GC, to give the conversion of 253fb and selectivity to 1243zf results shown in Table 2. The experiment was also repeated at 300 and 350° C.

TABLE 3

Results for 253fb dehydrochlorination to 1243zf with ZnO/Cr$_2$O$_3$ catalyst

| Pre-fluorinated | HF flow ml/min | 253fb flow ml/min | 250° C. 253fb Conversion % | 250° C. 1243zf Selectivity % | 300° C. 253fb Conversion % | 300° C. 1243zf Selectivity % | 350° C. 253fb Conversion % | 350° C. 1243zf Selectivity % |
|---|---|---|---|---|---|---|---|---|
| Yes | 31 | 5.3 | 41.20 | 85.15 | 93.50 | 99.47 | 93.57 | 99.29 |
| Yes | 31 | 5.1 | 40.19 | 85.00 | 87.96 | 99.01 | 98.02 | 99.79 |

TABLE 3-continued

Results for 253fb dehydrochlorination to 1243zf with ZnO/Cr$_2$O$_3$ catalyst

| | HF | 253fb | 250° C. | | 300° C. | | 350° C. | |
|---|---|---|---|---|---|---|---|---|
| Pre-fluorinated | flow ml/min | flow ml/min | 253fb Conversion % | 1243zf Selectivity % | 253fb Conversion % | 1243zf Selectivity % | 253fb Conversion % | 1243zf Selectivity % |
| No | 0 | 4.1 | 6.93 | 93.30 | 8.74 | 90.32 | 5.53 | 77.57 |
| No | 0 | 4.7 | 1.94 | 83.70 | 6.01 | 86.08 | 7.34 | 82.15 |
| Yes | 0 | 5.1 | | | 22.00 | 98.03 | | |
| Yes | 0 | 4.9 | | | 19.57 | 97.57 | | |

Overall there was an improvement in the conversion and slightly higher selectivity to 1243zf when the catalyst was pre-fluorinated and 253fb co-fed with HF.

EXAMPLE 3

Azeotrope Identification

A binary azeotrope between HF and 253fb was identified by a study of the vapour-liquid equilibrium of binary mixtures over a temperature range of −25° C. to +70° C. using a constant volume apparatus.

The experimental data were measured in a static constant volume apparatus consisting of a vessel of precisely known internal volume (32.57 ml) located in a temperature-controlled metal block. A magnetic stirring device was located inside the vessel. Refrigerated fluid was passed through the block to allow precise control of temperature inside the vessel. The cell was evacuated then known amounts of compositions of HF and 253fb were charged to the cell. The cell was then varied stepwise from about −25° C. to +70° C. At each step the cell temperatures and pressure were logged and recorded when stable conditions were reached.

Figure 2:
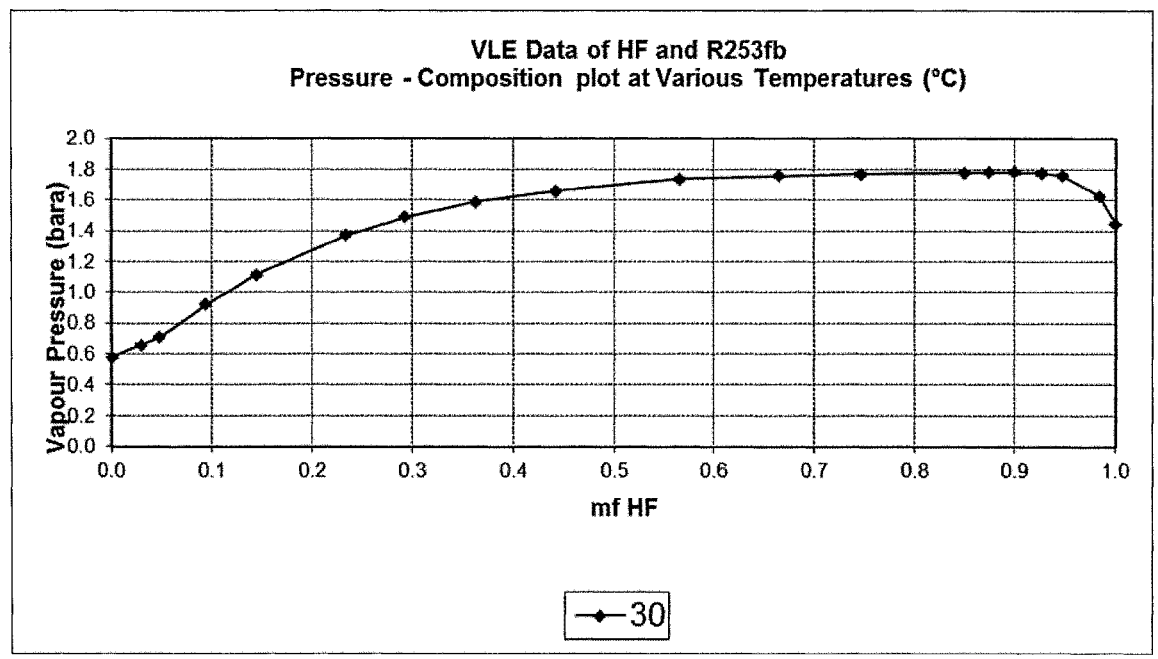
Figure 3:
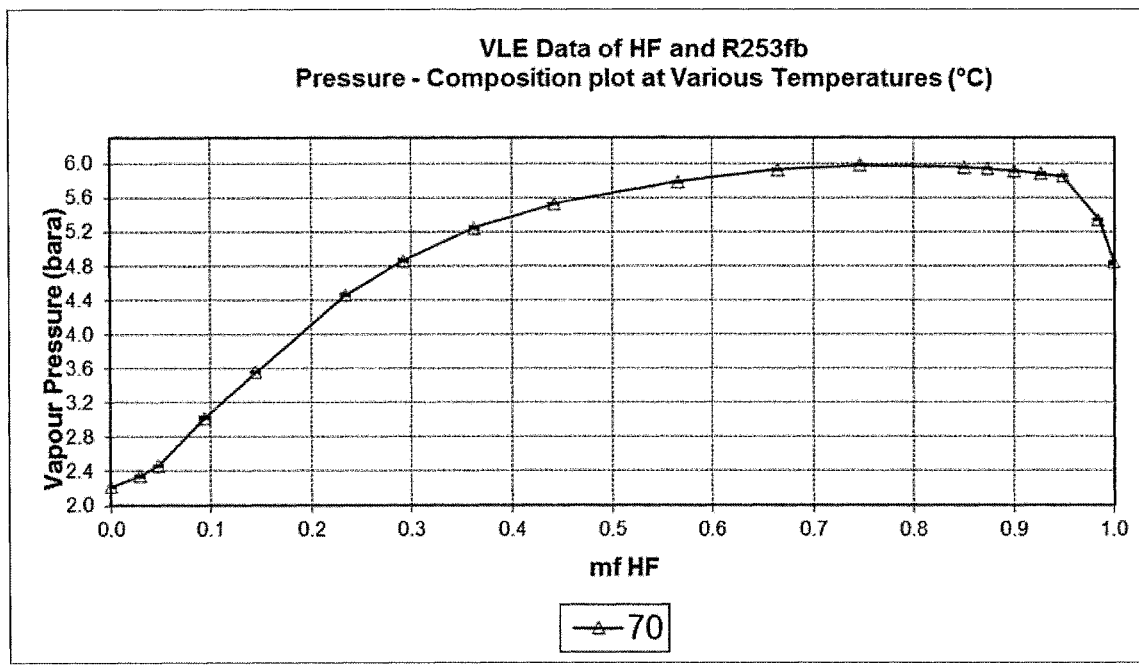

The compositions studied are given in Table 3 below. The phase behaviour of these compositions at three exemplary temperatures, being −25° C., +30° C. and +70° C. is illustrated in FIGS. 1 to 3. The graphs in FIGS. 1 to 3 show that a constant vapour pressure is reached at compositions wherein HF is present in an amount of from about 55 mol % to about 95 mol % and 253fb is present in an amount of from about 45 mol % to about 5 mol %, which is consistent with what would be expected of azeotropic compositions. This trend is evidenced across all temperature ranges tested.

TABLE 3

| Mole fraction R253fb | Mole fraction HF | % w/w HF |
|---|---|---|
| 1.000 | 0.000 | 0.000 |
| 0.971 | 0.029 | 0.452 |
| 0.952 | 0.048 | 0.752 |
| 0.906 | 0.094 | 1.546 |
| 0.855 | 0.145 | 2.488 |
| 0.766 | 0.234 | 4.417 |
| 0.708 | 0.292 | 5.867 |
| 0.638 | 0.362 | 7.902 |
| 0.558 | 0.442 | 10.696 |
| 0.558 | 0.442 | 10.696 |
| 0.434 | 0.566 | 16.442 |
| 0.335 | 0.665 | 23.058 |
| 0.253 | 0.747 | 30.790 |
| 0.150 | 0.850 | 46.130 |
| 0.126 | 0.874 | 51.102 |
| 0.100 | 0.900 | 57.743 |
| 0.073 | 0.927 | 65.671 |
| 0.052 | 0.948 | 73.330 |

TABLE 3-continued

| Mole fraction R253fb | Mole fraction HF | % w/w HF |
|---|---|---|
| 0.016 | 0.984 | 90.390 |
| 0.000 | 1.000 | 100.000 |

EXAMPLE 4

A feed composition of HF and 253fb was charged to a whitey bomb, agitated, and placed in a chilled bath at constant temperature. The system was left overnight to achieve thermal and phase equilibrium. Consecutive samples were withdrawn from the base of the whitey bomb, slowly, every half an hour over a total period of 4 hours so as not to disturb the phase equilibrium in the bomb, and analysed to determine HF concentration. The results shown in Table 4 demonstrate the separation of HF and 253fb into two liquid phases.

| Initial charge | 99.7 g |
|---|---|
| Feed composition | 81.91 mol % HF |
| Temp | −25° C. |

TABLE 4

| Sample | Sample mass (g) | Mol Frac HF |
|---|---|---|
| 1 | 8.2 | 33.91* |
| 2 | 7.2 | 16.64 |
| 3 | 25.9 | 17.53 |
| 4 | 8.2 | 15.06 |
| 5 | 12.3 | 96.11 |
| 6 | 8.5 | 97.53 |
| 7 | 7.8 | 97.47 |
| 8 | 10.4 | 97.01 |
| 9 | Residual mass | Not analysed |

*Note, the geometry of the offtake line at the base of the bomb means that the initial contents of the offtake line do not reach phase equilibrium with the bulk contents within the bomb. This results in an initial sample which contains high levels of HF.

The invention claimed is:

1. A process for preparing 3,3,3-trifluoropropene (1243zf), the process comprising:
    (a) fluorinating $CCl_3CH_2CH_2Cl$ (250fb) to produce a reaction product comprising $CF_3CH_2CH_2Cl$ (253fb) in the liquid phase conducted at a temperature from 20° C. to 100° C., in a first reactor, using HF as the fluorinating agent; and
    (b) dehydrohalogenating 253fb to produce 1243zf in the vapour phase, conducted at a temperature from 250° C. to 350° C., in the presence of a catalyst in a second reactor.

2. A process according to claim 1, wherein the catalyst used in step (b) comprises activated carbon, alumina and/or chromia or zinc/chromia.

3. A process according to claim 1, wherein the catalyst used in step (b) is activated carbon, Pd/carbon, Pt/carbon, Au/carbon, Pd/alumina, Ni/alumina, Pt/alumina, Cr/alumina or Zn/chromia.

4. A process according to claim 1, wherein the catalyst used in step (b) is pre-fluorinated.

5. A process according to claim 1, wherein the process in step (b) is continuous.

6. A process according to claim 1, wherein step (b) is conducted at a temperature of from about 250° C. to about 300° C.

7. A process according to claim 2, wherein the catalyst used in step (b) comprises activated carbon and the process of step (b) is conducted at a temperature from about 250° C. to about 300° C.

8. A process according to claim 4, wherein the catalyst used in step (b) is a pre-fluorinated Zn/chromia catalyst and the process of step (b) is conducted at a temperature from about 250° C. to about 350° C.

9. A process according to claim 1, wherein in step (b) HF is co-fed with 253fb.

10. A process according to claim 1, wherein the reaction product comprising 253fb produced in step (a) is subjected to one or more purification steps before step (b).

11. A process for preparing 3,3,3-trifluoropropene (1243zf), the process comprising:
   (a) fluorinating $CCl_3CH_2CH_2Cl$ (250fb) to produce a reaction product comprising $CF_3Cl_2CH_2Cl$ (253fb) in the liquid phase in a first reactor, using HF as the fluorinating agent; and
   (b) dehydrohalogenating 253fb to produce 1243zf in a second reactor;
   wherein the reaction product comprising 253fb produced in step (a) is subjected to one or more purification steps before step (b).

12. A process according to claim 9, wherein the purification steps comprise subjecting product stream from step (a) to distillation to remove or reduce the concentration of HCl and then phase separation to separate HF from the product stream comprising 253fb and optionally passing the stream comprising 253fb through a $H_2SO_4$ scrubber.

13. A process according to claim 11, wherein HF is recycled to step (a).

14. A process according to claim 1, wherein the first reactor is connected to a rectifying column.

15. A process according to claim 14, wherein at least part of the HF is introduced into the first reactor via the top of the rectifying column.

16. A process according to claim 11, wherein unused HF is separated from the reaction product produced in step (a) and recycled to the first reactor.

17. A process according to claim 1, wherein step (a) is conducted at a temperature of from about 40 to about 70° C.

18. A process according to claim 1, wherein step (a) is conducted at a pressure of from about 200 kPa to about 700 kPa.

19. A process according to claim 1, wherein step (a) is conducted in the presence of a polymerisation inhibitor and/or retarder.

20. A process according to claim 19, wherein the polymerisation inhibitor and/or retarder is selected from cyclic ketone or quinone-based aromatic compounds, nitro- or nitrogen-containing compounds, and sulphur-containing compounds.

21. A process according to claim 20, wherein the cyclic ketone is cyclobutanone or cyclohexanone or a mixture thereof.

22. A process according to claim 1, wherein step (a) is conducted in the presence of a Lewis acid catalyst.

23. A process according to claim 22, wherein the catalyst is $SnCl_4$.

24. A process according to claim 1, wherein step (a) is a semi-continuous reaction.

* * * * *